United States Patent
Chandler

(10) Patent No.: US 9,348,342 B1
(45) Date of Patent: May 24, 2016

(54) WATER SUPPLY ASSEMBLY FOR AN AUTOCLAVE

(71) Applicant: VISTA RESEARCH GROUP, LLC, Ashland, OH (US)

(72) Inventor: James W. Chandler, Ashland, OH (US)

(73) Assignee: VISTA RESEARCH GROUP, LLC, Ashland, OH (US)

( * ) Notice: Subject to any disclaimer, the term of this patent is extended or adjusted under 35 U.S.C. 154(b) by 0 days.

(21) Appl. No.: 14/586,689

(22) Filed: Dec. 30, 2014

(51) Int. Cl.
| | |
|---|---|
| A61L 2/08 | (2006.01) |
| F22B 5/00 | (2006.01) |
| F16K 11/00 | (2006.01) |
| C10B 51/00 | (2006.01) |
| F24D 3/00 | (2006.01) |
| G05D 9/02 | (2006.01) |
| A61L 2/07 | (2006.01) |
| G05D 7/01 | (2006.01) |

(52) U.S. Cl.
CPC ... *G05D 9/02* (2013.01); *A61L 2/07* (2013.01); *G05D 7/0146* (2013.01)

(58) Field of Classification Search
CPC .............................. A61L 2/00; A61C 19/002
USPC ................... 422/26, 517, 530, 298–299, 307; 122/13.01, 459, 460; 137/241; 202/94; 237/58
See application file for complete search history.

(56) References Cited

U.S. PATENT DOCUMENTS 3,303,837 A * 2/1967 Rither ...................... F24D 5/00
126/113

* cited by examiner

*Primary Examiner* — Monzer R Chorbaji
(74) *Attorney, Agent, or Firm* — Walker & Jocke

(57) ABSTRACT

A water supply assembly is provided that includes a support cap, an inlet port and a valve assembly. The valve assembly includes a valve, an outlet port and a float. The support cap has a shape that is configured to cover a reservoir opening into a reservoir of an autoclave, which reservoir opening has a maximum inner diameter that is between 1.5 and 3.0 inches. The float has a shape that is operative to pass through the reservoir opening and into the reservoir when the support cap is placed on the autoclave and is supported by the autoclave in a position to cover the reservoir opening of the autoclave. When the support cap is placed over the reservoir opening, with the float positioned in the reservoir, the inlet port extends outside the reservoir. The float is operative to move from a first position to a second position responsive to a decrease in a water level in the reservoir which causes the valve to open and enable water provided to the inlet port to pass out of the outlet port and into the reservoir.

20 Claims, 7 Drawing Sheets

WATER SUPPLY ASSEMBLY FOR AN AUTOCLAVE

BACKGROUND

Autoclaves are apparatuses that are typically used to sanitize medical and dental tools. Autoclaves such as the Statim 2000 and 5000 autoclaves sold by SciCan Ltd of Toronto, Ontario, Canada, include a water reservoir mounted inside a housing of the autoclaves. Both the reservoir and the housing include openings at the top of the autoclaves in which water may be poured into the reservoir. Such openings typically include a removable screen cup which intercepts objects that accidently fall into the openings. Also, such autoclaves may include a removable cap to cover the opening into the reservoir. In addition, such autoclaves typically include a removable cassette in which articles such as tools may be placed to be sterilized. However, it should be appreciated that in other models of autoclaves, rather than having a cassette, such autoclaves may include an interior chamber having racks and/or drawers in which articles may be placed inside the autoclaves. During operation, an autoclave consumes water from its reservoir for use with generating steam that sanitizes the articles placed in the autoclave.

Autoclaves may benefit from improvements.

SUMMARY

The following is a brief summary of subject matter that is described in greater detail herein. This summary is not intended to be limiting as to the scope of the claims.

In one example embodiment of one or more inventions described herein, an apparatus is provided that comprises a water supply assembly for use with automatically providing water to a reservoir in an autoclave. The water supply assembly may include a support cap. The support cap may include a channel therethrough.

The water supply assembly may also include an inlet port in operative supported connection with the support cap and in fluid communication with the channel. In addition, the water assembly may include a valve assembly in operative supported connection with the support cap and in fluid communication with the channel.

The valve assembly may include a valve, at least one outlet port and a valve actuator (such as a float that is buoyant in water). In example embodiments where the valve actuator includes a float, such a float may be movable relative to the support cap between a first position and a second position. At the first position, the float causes the valve to close fluid communication between the at least one outlet port and the channel. At the second position, the float causes the valve to open fluid communication between the at least one outlet port and the channel.

In this described embodiment, the support cap has a shape that is configured to cover a reservoir opening into a reservoir of an autoclave, which autoclave is configured to consume water from the reservoir for use with sanitizing articles placed in the autoclave. In an example embodiment of the described water supply assembly, the valve actuator (such as a float) has a shape that is operative to pass through such a reservoir opening and into the reservoir when the support cap is placed on the autoclave and is supported by the autoclave in a position to cover the reservoir opening of the autoclave.

Also in this described example, when the support cap is placed over the reservoir opening (with the valve actuator such as a float positioned in the reservoir) the inlet port extends outside the reservoir. Such an inlet port for example may be connected to a water line so as to provide water to the water supply assembly.

In this described arrangement of the support cap on the autoclave, the valve actuator is operative responsive to a decrease in a water level in the reservoir to cause the valve to open and enable water provided to the inlet port to pass through the channel, out of the at least one outlet port and into the reservoir in order cause an increase in the water level in the reservoir. Also in this described arrangement of the support cap on the autoclave, the valve actuator is operative responsive to the increase in the water level in the reservoir to cause the valve to close and prevent water provided to the inlet port from passing through the channel, out of the at least one outlet port and into the reservoir.

In examples where the valve actuator includes a float, the float is operative to move from the described first position to the described second position responsive to a decrease in a water level in the reservoir which causes the valve to open and enable water provided to the inlet port to pass through the channel, out of the at least one outlet port and into the reservoir in order cause an increase in the water level in the reservoir. Also, the float is operative to move from the second position to the first position responsive to the resulting increase in the water level in the reservoir, which causes the valve to close and prevent further water provided to the inlet port from passing through the channel, out of the at least one outlet port and into the reservoir.

As discussed previously, some models of autoclaves may include a removable cap and screen cup that are adapted to cover and/or extend into the reservoir opening. With such autoclaves, the cap and screen cup may be removed from the reservoir opening and replaced with the described water supply assembly, which serves as both a replacement cap and a mechanism for automatically filling the reservoir with water.

In some embodiments, the inlet port may be in rotatable connection with the support cap at an axis of rotation. The inlet port includes an inlet port opening that is disposed radially from an axis of rotation. Thus, rotation of the inlet port is operative to move a location with respect to the autoclave at which a water supply line is connectable to the inlet port. This described feature enables a water line to be rotated around the inlet port in order to place the water line in a position that is preferable based on where a filtered water source may be located with respect to the autoclave.

In example embodiments, the autoclave that the support cap is configured to cover a reservoir opening thereof, will typically include a housing in which the reservoir is mounted. Such a housing may also enclose other components of the autoclaved such as the electronics, the sterilization chamber, portions of a cassette, and other elements that enable the autoclave to operate. Such a housing may have a housing opening adjacent the reservoir opening. Such reservoir openings and housing openings may be orientated to face upwardly from an upper surface of the housing of the autoclave. In some embodiments, the housing opening may have a maximum inner diameter that is larger than the maximum inner diameter of the reservoir opening. For such embodiments, the shape of the support cap may have a configuration that is operative to cover and extend into both the reservoir opening and the housing opening.

For example, the shape of the support cap may includes a stepped contour that includes consecutively wider first and second steps, wherein the first step is operative to extend into the reservoir opening and the second step covers the reservoir opening and/or housing opening. Also the stepped contour may include consecutively wider: the first step; the second step; and a third step, wherein when the first step extends into the reservoir opening, the second step extends into the housing opening and the third step covers the housing opening. Thus, the second step may be wider than the maximum inner diameter of the reservoir opening and the third step may be wider than the maximum inner diameter of the housing opening.

Also, it should be appreciated that the support cap may be configured such that when a water level in the reservoir increases sufficiently to cause the float in the reservoir to move from the second position to the first position, the support cap remains in a position that covers the opening into the reservoir and remains in supported contact with the autoclave (i.e., the support cap does not lift upwardly off of the housing of the autoclave).

To prevent the support cap from lifting upwardly when the water level rises, the first step of the support cap may have a configuration that is operative to become engaged in the reservoir opening. For example, the first step may include one or more annular ribs or a knurled textured surface that are operative to compressively engage with an inner wall (i.e., a reservoir neck) that bounds the reservoir opening. However, it should be appreciated that autoclaves may have other configurations and shapes for the openings to the reservoir and housing. Thus, the described support cap may have alternative contours that correspond to such configurations and shapes of the openings to the reservoir and housing of the autoclave in order to both cover the openings and prevent the support cap from lifting upwardly responsive to upward movement of the float. Alternatively or in addition, the support cap may be comprised of at least one of a dense thermoplastic, a stainless steel or a combination thereof that has a sufficient weight to prevent the support cap from lifting upwardly when a water level in the reservoir increases.

Other aspects will be appreciated upon reading and understanding the attached figures and description.

DETAILED DESCRIPTION

Figure 1:
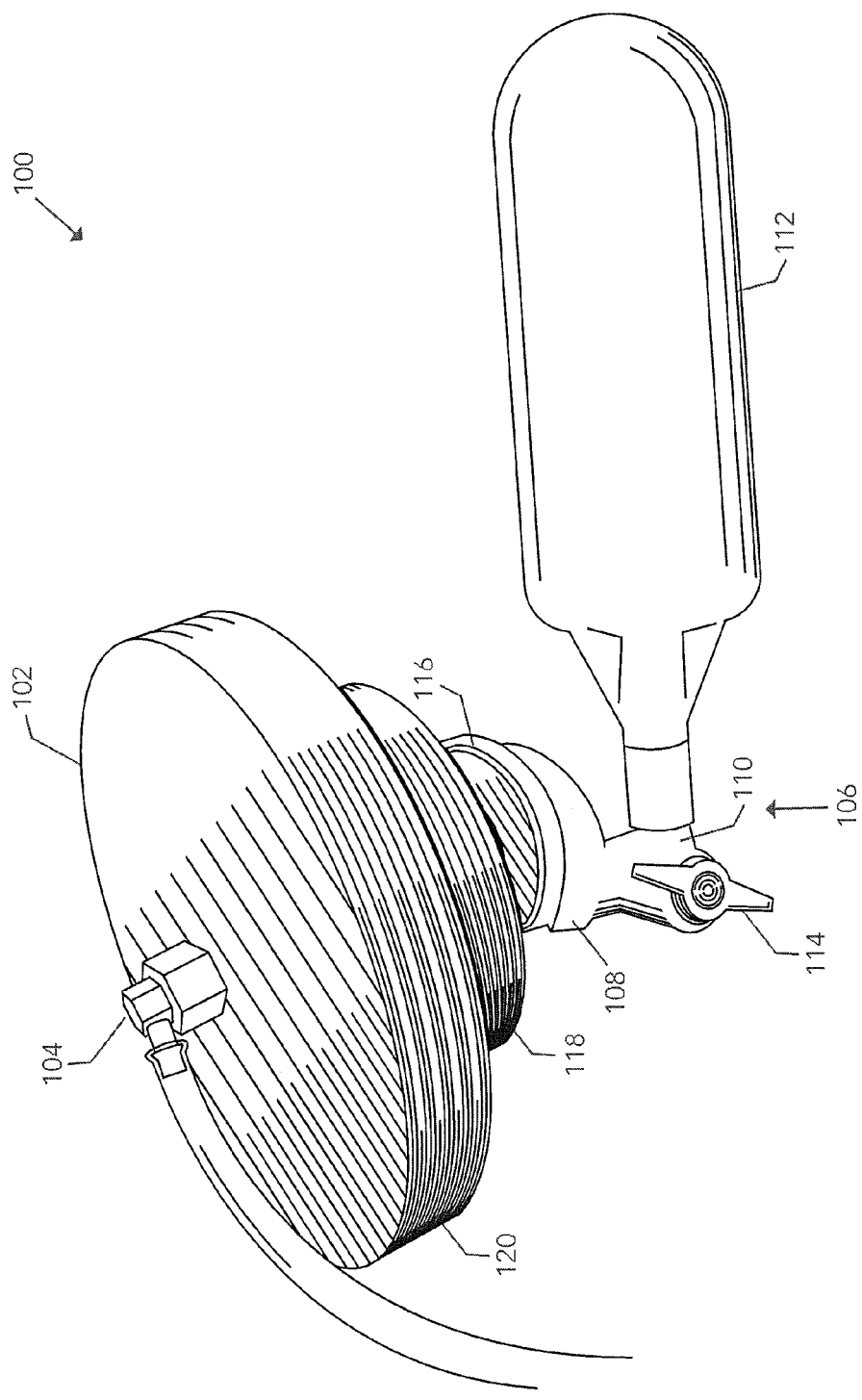
FIG. 1 is a perspective view of an example water supply assembly that facilitates automatically providing water to a reservoir in an autoclave.

Various technologies pertaining to a water supply assembly for an autoclave will now be described with reference to the drawings, where like reference numerals represent like elements throughout. In addition, several schematic diagrams of example systems are illustrated and described herein for purposes of explanation; however, it is to be understood that functionality that is described as being carried out by certain components may be performed by multiple components. Similarly, for instance, a component may be configured to perform functionality that is described as being carried out by multiple components.

With reference to FIG. 1, an example perspective view of a water supply assembly 100 that facilitates automatically providing water to a reservoir of an autoclave is illustrated. As will be described in more detail below the described water supply assembly 100 is configured to replace a cap to the reservoir of the autoclave in a manner that provides automatic refilling of the reservoir with water.

In an example embodiment, the assembly 100 includes a support cap 102. The assembly 100 also includes an inlet port 104 in operative supported connection with the support cap. In addition the assembly 100 includes a valve assembly 106 in operative supported connection with the support cap. The valve assembly includes a valve 108, at least one outlet port 110 and a valve actuator 122 (such as a pivoting and/or sliding float and associated linkages that operate the valve).

Figure 2:
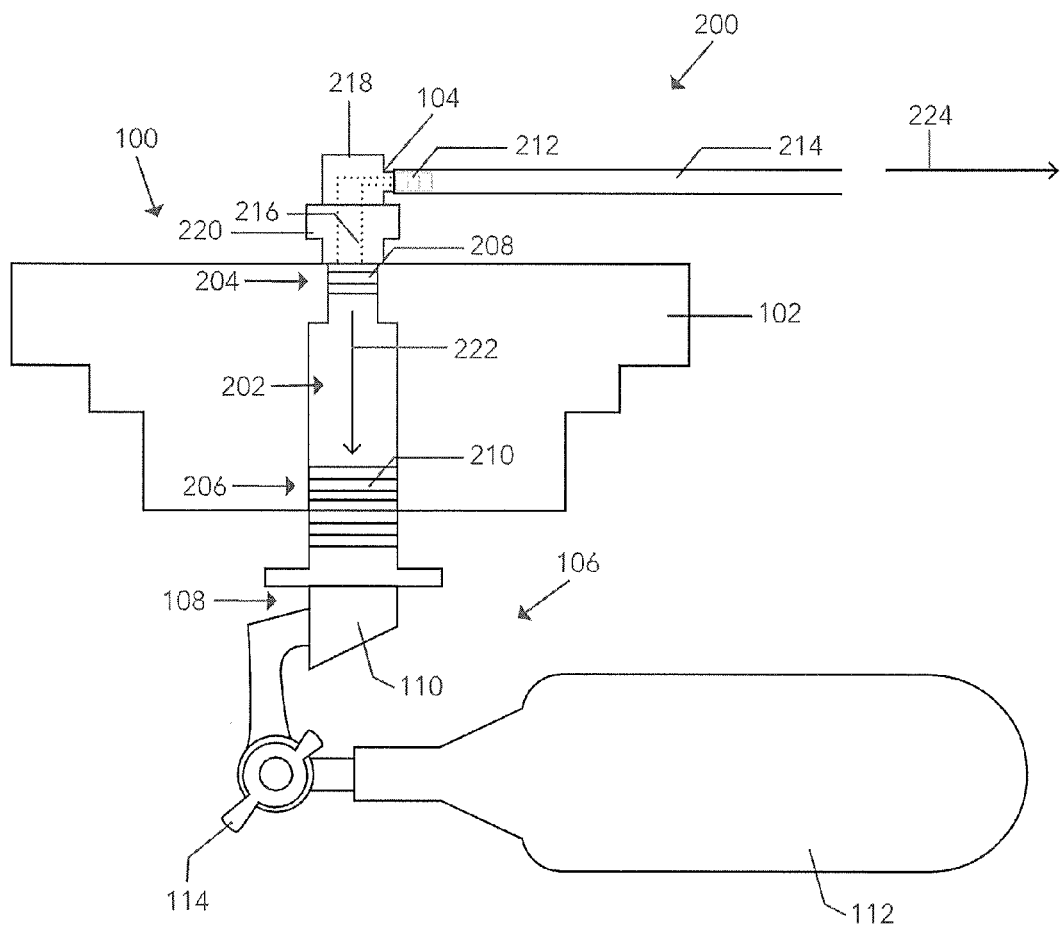
FIG. 2 is a schematic cross-sectional view of an example water supply assembly.

To better illustrate internal features, FIG. 2 shows a side cross-sectional view 200 of the assembly 100. The support cap 102 may include a channel 202 therethrough. Both the inlet port 104 and the valve assembly 106 may be in fluid communication with the channel 202. In this described example, the channel may correspond to a bore formed in a generally central portion of the support cap having opposed upper and lower threaded openings 204, 206. Threaded ends 208, 210 of the respective inlet port 104 and valve assembly 106 may be secured in the respective upper and lower threaded openings 204, 206 with suitable seals to form a water tight connection.

In example embodiments, the upper threaded opening 204 of the channel of the support cap may have 10-32" straight thread, whereas the lower threaded opening 206 of the channel of the support cap may have a ¼" NPT threaded area. However, it should be appreciated that the channel may have other sizes and diameters to accommodate other sizes of threaded inlet ports and valve assemblies as well as push-to-connect arrangements of such components.

In an example embodiment, the inlet port may include an external male coupler 212 that is operative to accommodate the connection of a water line 214 to the inlet port. Such an external male coupler 212 may correspond to a barbed projection having an opening to a channel 216 that extends through the inlet port to the channel 202 of the support cap. A water line (made out of a flexible rubber for example) may be mounted around the barbed projection to form a water tight and secure connection between the water line and the inlet port. For example the water line may be made from ¼" OD×⅛" ID polyurethane tubing or other sizes or types of tubing.

In this described embodiment, the male coupler 212 may be orientated to extend from an upper end 218 of the inlet port in a first direction 224 that is perpendicular to a second direction 222 that the channel 202 extends from the opposed threaded openings 204, 206 in the support cap. In addition in this described example, the upper end 218 may be in rotatable connection with a base end 220 of the inlet port, in order to enable the upper end 218, the male coupler 104, and connected water line 214 to swivel (i.e., rotate) about an axis of rotation that extends in the second direction 222. For example the male coupler 212 and inlet port 104 and may correspond to a ⅛" stainless steel hose barb that is threaded into a swivel hose barb fitting.

However, it should be appreciated that alternative embodiments may include other types of inlet ports such as fixed (non-rotating) ports, ports that have male or female couplers that extends at other angles (such as parallel to the second direction 202), and ports that have different styles of couplers (such as smooth or threaded projections) that are capable of connecting to a water line. For example, in an alternative embodiment, the inlet port may correspond to a female quick connect coupler that receives a male adapter mounted to the water line.

In example embodiments, the valve 108 of the valve assembly 106 may correspond to a pinch valve, a piston valve, or any other type of valve mechanism that can open and close the flow of water through the valve assembly and out the outlet port 110.

In an example embodiment, the valve actuator 112 may include a float that is buoyant in water. Such valve 108 may have a mechanical eccentric pinch valve design. Also, the valve assembly may include a wing nut 114 to enable the relative position of the float 112 to be adjusted on the valve assembly. This adjustment may be used to control the ultimate desired levels of water that causes the valve of the valve assembly to open and close without changing the float itself. Example floats may be full horizontal, modified vertical with a short horizontal float bulb, a ball float, or any other configuration of a float.

However, it should be appreciated that example embodiments may use other types of floats or valve actuators that can be configured to control a valve responsive to a water level. For example, a valve mechanism and/or a valve actuator may include a float switch, a limit switch, a reed switch, a solenoid or other (typically low voltage) signaling device.

Figure 3:
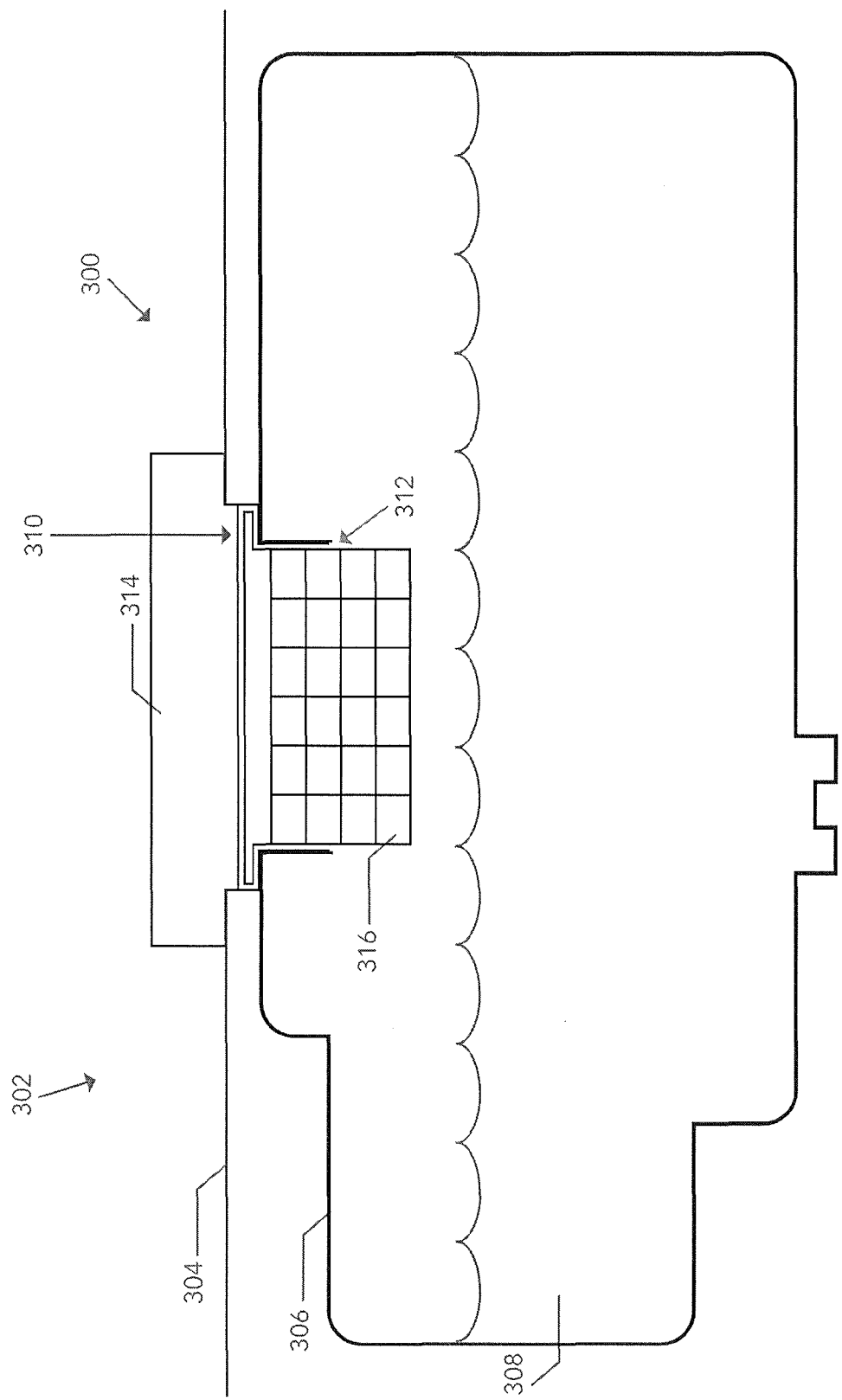
FIG. 3 is a schematic cross-sectional view of portions of an example autoclave.
Figure 4:
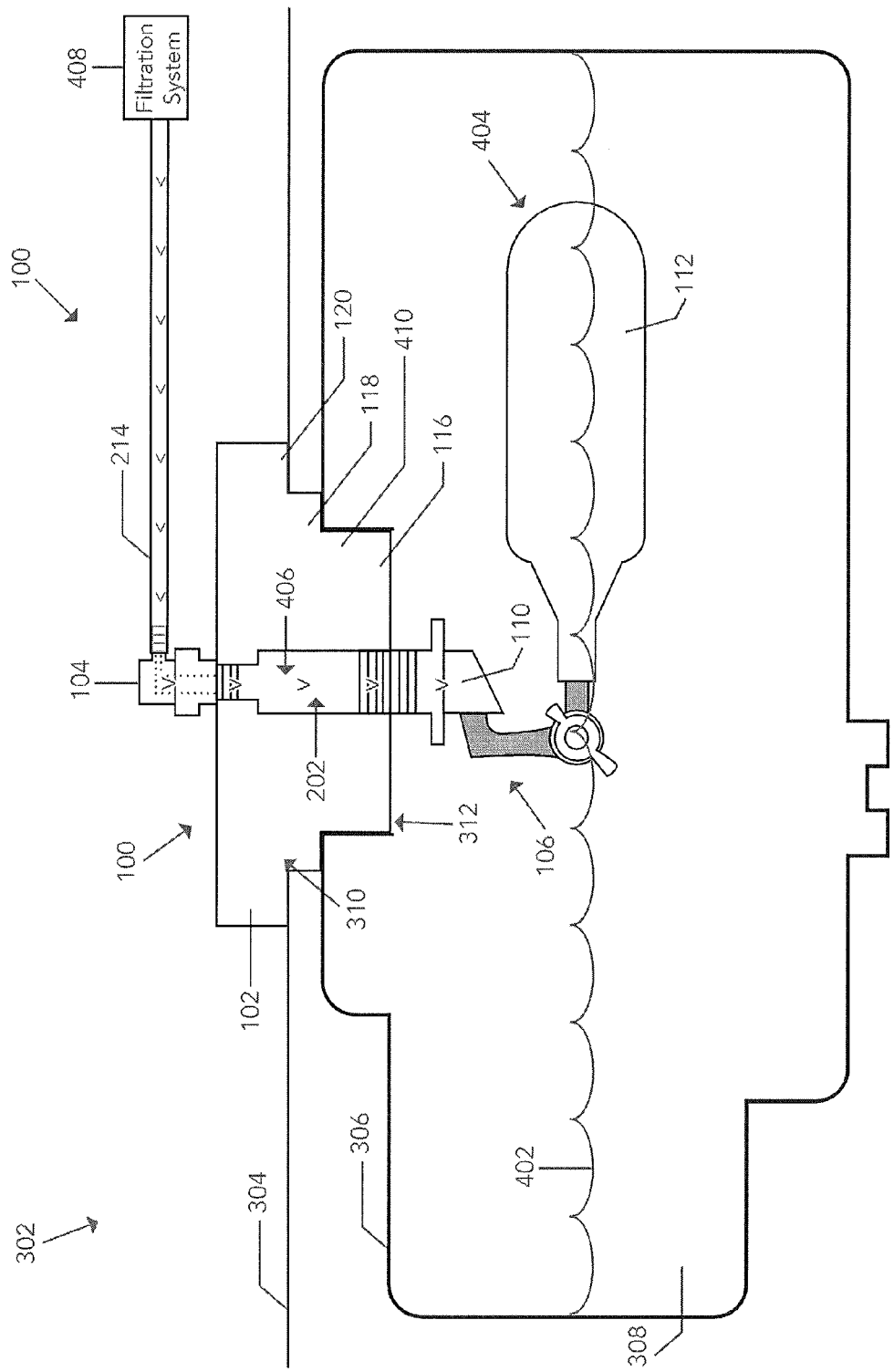
FIGS. 4-5 are schematic cross-sectional views of the example water supply assembly installed on an autoclave.
Figure 5:
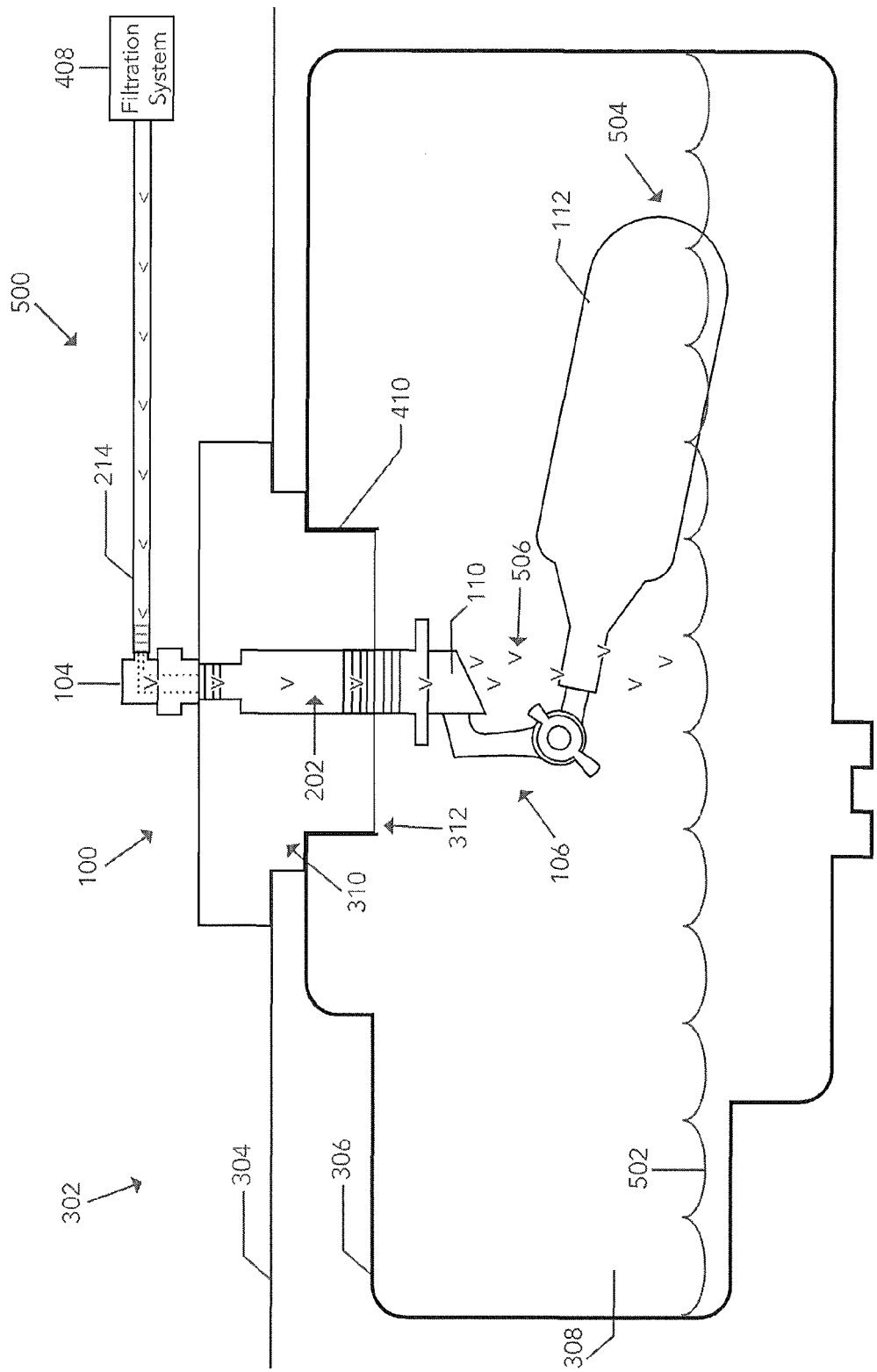

FIG. 3 illustrates a schematic view 300 of portions of an example autoclave 302. FIGS. 4 and 5 illustrate example views 400, 500 in which the described water supply assembly 100 may be used with the autoclave 302. As shown in FIG. 3, the autoclave 302 may include a housing 304 that encloses an internal reservoir 306 for water 308. Such reservoirs are typically comprised of a food grade polyethylene or polypropylene.

The housing 304 of the autoclave may be made from a rigid plastic (e.g. such as PVC) and/or metal (such as stainless steel) and may include an opening 310 above an opening 312 into the reservoir 306. The autoclave may also include a removable cap 314 that covers the opening 310 to the housing. In addition, such an autoclave may include a porous screen cup 316 that extends into the opening for use with capturing large objects that may accidentally fall through the opening 310 of the housing into the autoclave. To manually fill such an autoclave with water, a user may remove the cap 314 and pour water from a jug into the openings 310, 312, through the screen cup 316, and into the reservoir 306.

In order to automate this process, as shown in FIG. 4, the previously described cap 314 and screen cup 316 may be removed from the autoclave, and may be replaced with the described water supply assembly 100. The support cap 102 of the assembly may have a shape that is configured to cover both the opening 310 through the housing and the opening 312 into the reservoir 306. Also, the described valve assembly 106 with float may be supported by the support cap such that the float is buoyant in the water 308 in the reservoir and is operative to move relative to the support cap between a first position and a second position responsive to changes to the water level in the reservoir.

FIG. 4 illustrates a first water level 402 of the water 308 in the reservoir 306 that is sufficiently high to urge the float 112 upwardly to the first position 404. FIG. 5 illustrates a second water level 502 of the water 308 in the reservoir 306 that is sufficiently low to enable the float 112 (responsive to gravity) to move downwardly to the second position 504.

As shown in FIG. 4., movement of the float 112 to first position 404 relative to the support cap 102, causes the valve of the valve assembly 106 to close fluid communication between the at least one outlet port 110 and the channel 202.

Thus, in the first position 404 of the float, a water flow 406 from the water line 214 is prevented by the valve from filling the reservoir with water.

However, as shown in FIG. 5, movement of the float 112 to the second position 504 relative to the support cap 102, causes the valve to open fluid communication between the at least one outlet port 110 and the channel 202. Thus, in the second position 504 of the float, a water flow 506 from the water line 214 is permitted by the valve to flow out of the outlet port 110 into the reservoir 306.

In example embodiments, the opening 312 to the reservoir may have a neck 410 that is generally circular and may have a maximum inner diameter that is between 1.5 and 3.0 inches (such as about 2.15 inches). Consequently, it should be appreciated that the float 112 will have a shape that is operative to pass through the opening 312 into the reservoir when the support cap is placed on the autoclave and is supported by the autoclave in a position to cover the opening 312 of the reservoir. However, it should be appreciated that example water supply assemblies may be adapted to work with other models and types of autoclaves that may have smaller or larger openings into a reservoir for water.

Also, the water supply assembly may be configured such that when the support cap 102 is placed over the opening 312 to the reservoir (with the float positioned in the reservoir) the inlet port 104 is located outside the reservoir 306 and outside the housing 304. However, it should be appreciated that in alternative embodiments, the inlet port may be located out of the reservoir 306 but not out of the housing 304. For example the water line 214 may be routed inside the housing to another opening through the housing other than the opening 310 of the housing above the opening 312 to the reservoir.

It should be appreciated with respect to FIGS. 4 and 5 that the float 312 is operative to move from the first position to the second position responsive to a decrease in the water level in the reservoir caused by the autoclave withdrawing water from the reservoir for use with sanitizing articles in the autoclave. This decrease in the water level thus causes the valve of the water supply assembly to open and enable water provided to the inlet port to pass through the channel, out of the at least one outlet port and into the reservoir in order cause an increase in the water level in the reservoir. As the water level increases in the reservoir, the float is operative to move from the second position to the first position, which causes the valve to close and prevent water provided to the inlet port to pass through the channel, out of the at least one outlet port and into the reservoir.

It should also be noted that autoclave reservoirs may also include additional mechanisms that operate responsive to the water level in the reservoir. For example, an autoclave may include a water presence or pressure sensor that is operative to provide an electronic signal (to a processor of the autoclave) that is indicative of when the water level in the reservoir is too low to operate the autoclave to sterilize articles. In addition, autoclaves may include other sensor, such as a water purity sensor that provides an electrical signal (to the processor of the autoclave) that is indicative of when the purity of the water is outside a range suitable for the operation of the autoclave.

As illustrated in FIGS. 4 and 5, in example embodiments, the water line 214 may be configured to provide pressured water that has passed through one or more filtration systems 408. Examples of filtration systems that may be used to provide filtered water through a water line to the described water supply assembly include the VistaClear system provided by Vista Research Group of Ashland, Ohio. Further examples of filtration systems that may be used supply water to the water supply assembly are shown in U.S. Pat. No. 6,423,219 issued Jul. 23, 2002, which is hereby incorporated herein in its entirety.

It should also be noted that a typical dental office or doctors office may include several autoclaves, which may include one of the described water system assemblies in place of their stock reservoir caps. In such embodiments, the same water filtration system 408 may include a water line that branches out and connects to each of the inlet ports of the water system assemblies for each of the autoclaves.

Referring back to FIG. 4, it should be appreciated that when the float is in the second position 404 and the valve becomes closed, the float will reach a point where it can no longer move (e.g., pivot or slide) upwardly relative to the support cap. Thus, upwardly directed forces caused by the buoyancy of the float may also act on the support cap. In an example embodiment, the support cap may be configured such that when a water level in the reservoir increases sufficiently to cause the float in the reservoir to move from the second position to the first position, the support cap remains in a position that covers the opening into the reservoir and remains in supported contact with the autoclave. In other words the support cap is configured not to lift or pivot upwardly from the autoclave when the float moves upwardly in the reservoir.

In order to prevent the support cap from moving upwardly as the water level in the reservoir increases, the support cap may include a sufficient weight and or locking features which maintain the support cap in a stationary position over the reservoir and housing openings. For example the support cap may be constructed of a suitably thick and dense thermoplastic and/or a stainless steel that provides the support cap with sufficient weight to resist moving responsive to the upward water pressure acting on the float. Examples of thermoplastics that may be used to form the support cap include (PVC or CPVC).

In an example embodiment, the weight of the support cap (such as shown in FIG. 1) may be between 4-16 ounces (such as about 6.0 ounces) depending on the buoyancy factor of the float used in a particular application of the assembly and depending on whether the neck of the opening of the reservoir provides a compressive force to hold the support cap in place on the autoclave. However, it should be appreciated that alternative embodiments of the support cap may have other sizes and weights in order to prevent the support cap from lifting upwardly when the water level in the reservoir increases. For example, a large float bulb would create much greater lifting potential than a smaller bulb, thus heavier support caps may be used in such cases.

In an example embodiment, the shape of the support cap may have features that enable the support cap to limit evaporation of water from the reservoir and/or that assist in preventing the support cap from lifting upwardly when the water level in the reservoir rises. For example, as illustrated in FIG. 1, the shape of the support cap includes a stepped contour that includes consecutively wider: the first step 116; the second step 118; and a third step 120. As shown, in FIG. 3. the first step 116 has a shape that extends into the reservoir opening 312, while the second step 118 has a shape that extends into the housing opening 310, and while the third step 120 covers the housing opening 310 and rests on an outside surface of the housing 304 that surrounds the housing opening 310.

Also, in this example, the second step 118 is wider than the maximum inner diameter of the reservoir opening, wherein the third step is wider than the maximum inner diameter of the housing opening. With an autoclave that has a generally circular reservoir opening with a diameter of about 2.2 inches and a generally circular housing opening with a diameter of about 2.7 inches, an example support cap may have a generally circular first step with a diameter of about 2.159 inches, a generally circular second step with a diameter of about 2.672 inches and a generally circular third step with a diameter of about 3.5 inches.

However, it should be noted that alternative embodiments may have other sizes and shapes for one or more steps of the support cap, depending on the sizes of the reservoir and housing openings of the autoclave and the desired tightness of the fit between the described steps and reservoir and/or housing openings.

Also, it should be appreciated that in some embodiments, a support cap may only include a first and second step, where the first step extends into both the housing opening and the reservoir opening and the second step extends outside of housing opening and rests on the portions of the housing that surround the housing opening.

Also, it should be appreciated that one or more of the described steps of the support cap may have shapes other than circular shapes. For example, the first step may be partially oval and elongated in one direction by an amount that is equal to greater than the diameter of the reservoir opening and/or the second step may be partially oval and elongated in one direction by an amount that is equal to greater than the diameter of the housing opening. Such a contour of the first step may become compressively engage with the neck of the reservoir that surrounds the reservoir opening. Likewise such a contour of the second step may become compressively engage with portions of the housing that bound the housing opening.

It should also be noted that in some embodiments of autoclaves, the reservoir opening and/or the housing opening may not be perfectly circular, an example support cap may have circular first and/or second steps that are slightly wider in diameter than the narrowest inner width of the reservoir opening and/or housing opening in order to produce the previously described compressive engagement with the reservoir and/or housing of the autoclave.

Figure 6:
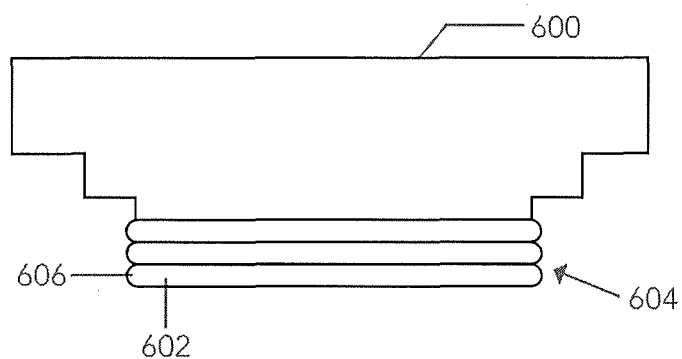
FIGS. 6 and 7 show an alternative contours for portions of the support cap.
Figure 7:
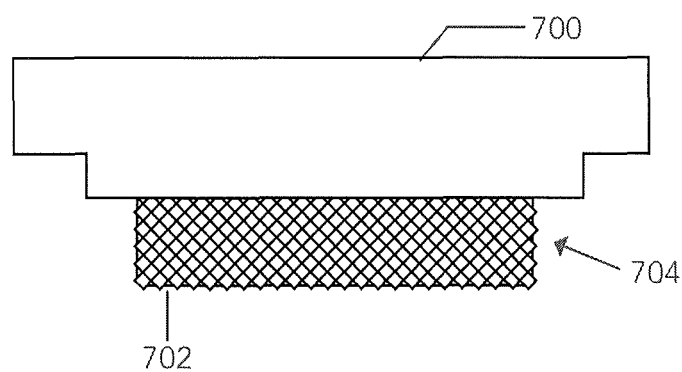

As shown in FIG. 1, the contours of the first step 116 may be generally smooth. However, it should be noted that in alternative embodiments, the circumferential outer surfaces of the first step may have other contours that aid in compressively engaging with the reservoir opening of an autoclave. For example as shown in FIG. 6, an alternative reservoir cap 600 may have a first step 602 that has circumferential outer surfaces 604 having a plurality of annular ribs 606. Also, for example as shown in FIG. 7, an alternative reservoir cap 700 may have a first step 702 that with circumferential outer surfaces 704 having a knurled surface texture. Such ribs or knurled texture may extend in positions that are operative to be compressively gripped by the inner walls of the neck of the reservoir opening of an autoclave.

However, it should be noted that in each of these described embodiments, in which a compressive connection is formed between the support cap and a portion of the autoclave (such as the reservoir or housing), the support cap may still be readily inserted and removed by hand from the autoclave without the use of tools.

Although not shown in the drawings, it should be appreciated that example embodiments of the described water supply assembly and/or associated water line, may include an in-line back flow prevention device, such as a dual check valve to prevent back flow. In addition it should be appreciated that the described water supply assembly may be adapted for use to fill and control the liquid level in other types of atmospheric tanks that may have a generally flat filler opening operative to accept a support cap having a valve assembly (e.g., fish tanks, laboratory water batch tanks, or any other corresponding type of reservoir).

It should also be noted that the described water supply assembly may have the following capabilities: Installs and uninstalls without tools; Has no hard physical attachment to the autoclave (e.g. no screws, threads, brackets, etc); Saves labor and time for attendants by avoiding manual filing of autoclaves with heavy bottles of water; Provides no spills as can occur when manually pouring from a water bottle and not being able to see the filler hole clearly; and Covers the reservoir and/or housing opening in order to help minimize evaporation of water from the reservoir.

Figure 8:
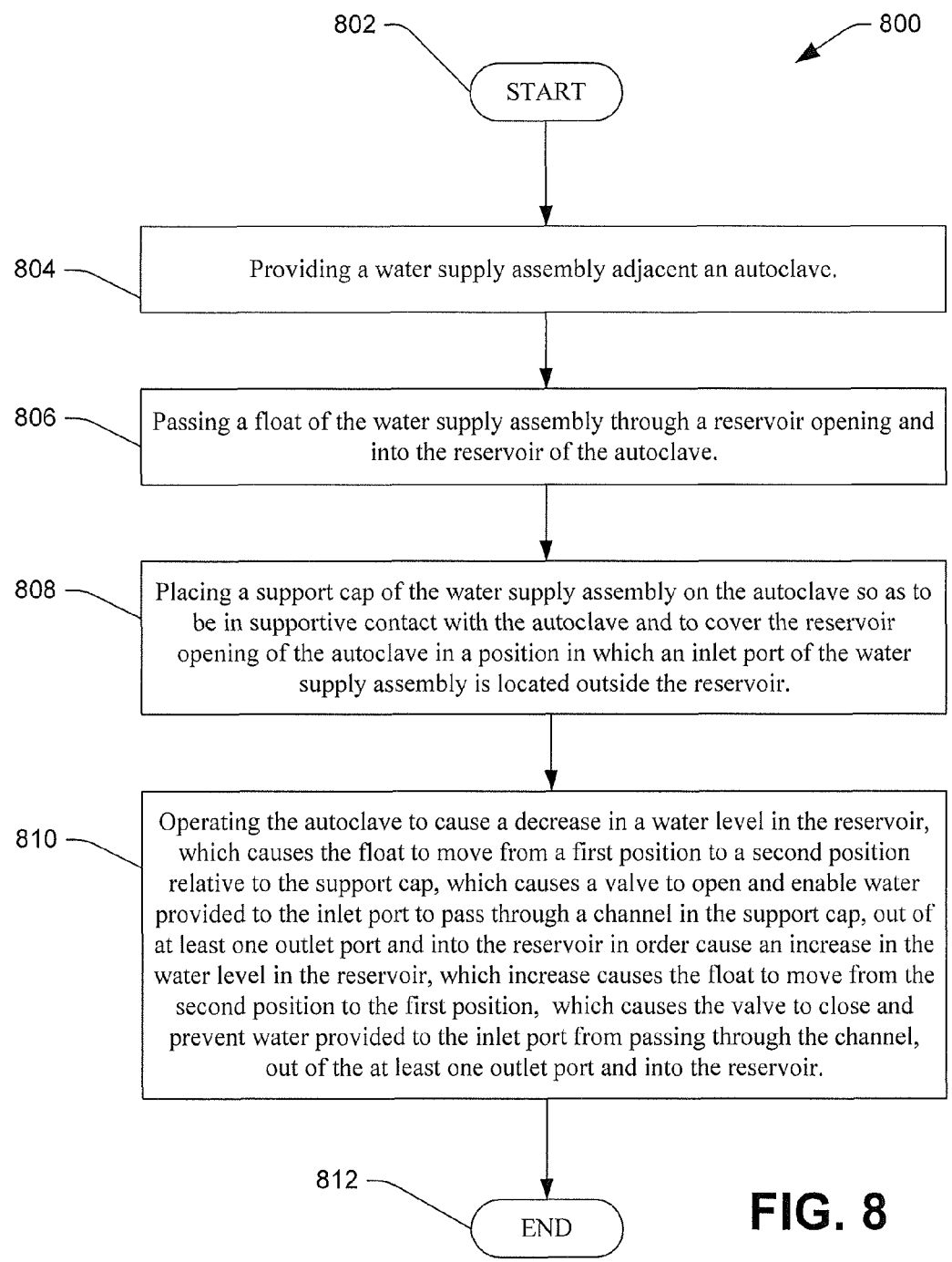
FIG. 8 is flow diagram that illustrates an example methodology that facilitates automatically providing water to a reservoir in an autoclave.

With reference now to FIG. 8, an example methodology is illustrated and described. While the methodology is described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Referring now to FIG. 8, a methodology 800 that facilitates automatically providing water to an autoclave is illustrated. The methodology 800 begins at 802, and at 804 comprises providing a water supply assembly (such as the water supply assemblies described previously) adjacent an autoclave. The methodology 800 may also include at 806 passing an valve actuator (such as a float) of the water supply assembly through a reservoir opening and into a reservoir of the autoclave. In addition the methodology 800 may include at 808 placing a support cap of the water supply assembly on the autoclave so as to be in supportive contact with the autoclave and to cover the reservoir opening of the autoclave in a position in which an inlet port of the water supply assembly is located outside the reservoir.

In this described example the methodology 800 may also include at 810 operating the autoclave to cause a decrease in a water level in the reservoir, which causes the float to move from a first position to a second position relative to the support cap, which causes a valve to open and enable water provided to the inlet port to pass through a channel in the support cap, out of at least one outlet port and into the reservoir in order cause an increase in the water level in the reservoir, which increase causes the float to move from the second position to the first position, which causes the valve to close and prevent water provided to the inlet port to pass through the channel, out of the at least one outlet port and into the reservoir. At 812 the methodology may end.

In this described example, the methodology may also comprise additional and/or optional steps. For example prior to passing the float of the water supply assembly into the reservoir, the methodology may include removing a cap from the housing opening and/or a screen cup from the reservoir opening to enable the float to be inserted into the reservoir opening. In addition as discussed previously, the support cap may be configured such that when a water level in the reservoir increases sufficiently to cause the float in the reservoir to move from the second position to the first position, the support cap remains in the position that covers the opening into the reservoir and is in supportable contact with the autoclave.

In order to use the described water supply assembly to provide water into an autoclave, the methodology may also include attaching a water supply line to the inlet port. Also, the methodology may include rotating the inlet port to move a location of the water supply line with respect to the autoclave.

In example embodiments, the methodology may include placing the support cap on the autoclave so as to cover both the reservoir opening and a housing opening of a housing the encloses the reservoir. Also as discussed previously, the described support cap may include a stepped contour that includes consecutively wider first and second steps. Thus the methodology may include placing the support cap on the autoclave such that the first step extends into the reservoir opening. Also in embodiments where the shape of the support cap includes a stepped contour that includes consecutively wider first step, second step, and third step, when the first step is placed so as to extend into the reservoir opening, the second step extends into the housing opening and the third step covers the housing opening It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. An apparatus comprising:
a water supply assembly, wherein the water supply assembly includes:
a support cap, wherein the support cap includes:
a channel therethrough;
an inlet port in operative supported connection with the support cap and in fluid communication with the channel;
a valve assembly in operative supported connection with the support cap and in fluid communication with the channel,
wherein the valve assembly includes a valve, at least one outlet port and a valve actuator,
wherein the support cap has a shape that is configured to cover a reservoir opening into a reservoir of an autoclave,
which autoclave is configured to consume water from the reservoir for use with sanitizing articles placed in the autoclave,
wherein the valve actuator has a shape that is operative to pass through the reservoir opening and into the reservoir when the support cap is placed on the autoclave and is supported by the autoclave in a position to cover the reservoir opening of the autoclave,
wherein when the support cap is placed on the autoclave and covers the reservoir opening with the float positioned in the reservoir:
the inlet port extends outside the reservoir;
the valve actuator is operative responsive to a decrease in a water level in the reservoir to cause the valve to open and enable water provided to the inlet port to pass through the channel, out of the at least one outlet port and into the reservoir in order to cause an increase in the water level in the reservoir,
the valve actuator is operative responsive to the increase in the water level in the reservoir to cause the valve to close and prevent water provided to the inlet port from passing through the channel, out of the at least one outlet port and into the reservoir.

2. The assembly according to claim 1, wherein the valve actuator includes a float that is buoyant in water,
wherein the float is movable relative to the support cap between:
a first position at which the float causes the valve to close fluid communication between the at least one outlet port and the channel; and a second position at which the float causes the valve to open fluid communication between the at least one outlet port and the channel, wherein the float has a shape that is operative to pass through the reservoir opening and into the reservoir when the support cap is placed on the autoclave and is supported by the autoclave in a position to cover the reservoir opening of the autoclave, wherein when the support cap is placed on the autoclave and covers the reservoir opening with the float positioned in the reservoir:

the float is operative to move from the first position to the second position responsive to a decrease in a water level in the reservoir which causes the valve to open and enable water provided to the inlet port to pass through the channel, out of the at least one outlet port and into the reservoir in order cause an increase in the water level in the reservoir, the float is operative to move from the second position to the first position responsive to the increase in the water level in the reservoir which causes the valve to close and prevent water provided to the inlet port to pass through the channel, out of the at least one outlet port and into the reservoir.

3. The apparatus according to claim 1, further comprising the autoclave, wherein the autoclave includes a screen cup adapted to extend into the reservoir opening, wherein the screen cup is removable from the reservoir opening to enable the float to be inserted into the reservoir opening, wherein the reservoir opening has a maximum inner diameter that is between 1.5 and 3.0 inches.

4. The apparatus according to claim 1, wherein the inlet port is in rotatable connection with the support cap at an axis of rotation, wherein the inlet port includes an inlet port opening that is disposed radially from an axis of rotation, wherein rotation of the inlet port is operative to move a location with respect to the autoclave at which a water supply line is connectable to the inlet port.

5. The apparatus according to claim 1, wherein the autoclave that the support cap is configured to cover a reservoir opening thereof, includes a housing in which the reservoir is mounted, wherein the housing includes a housing opening adjacent the reservoir opening, wherein the housing opening has a maximum inner diameter that is larger than the maximum inner diameter of the reservoir opening, wherein the shape of the support cap has a configuration that is operative to cover both the reservoir opening and the housing opening, wherein the support cap is configured such that when a water level in the reservoir increases sufficiently to cause the float in the reservoir to move from the second position to the first position, the support cap remains in a position that covers the opening into the reservoir and remains in supported contact with the housing of the autoclave.

6. The apparatus according to claim 5, wherein the shape of the support cap includes a stepped contour that includes consecutively wider first and second steps, wherein the first step is operative to extend into the reservoir opening.

7. The apparatus according to claim 6, wherein the shape of the support cap includes a stepped contour that includes consecutively wider the first step, the second step, and a third step, wherein when the first step extends into the reservoir opening, the second step extends into the housing opening and the third step covers the housing opening, wherein the second step and is wider than the maximum inner diameter of the reservoir opening, wherein the third step is wider than the maximum inner diameter of the housing opening.

8. The apparatus according to claim 6, wherein the first step has a configuration that is operative to become compressively engaged in the reservoir opening.

9. The apparatus according to claim 6, the first step includes at least one annular rib that compressively engages with a neck of the reservoir that surrounds the reservoir opening.

10. The apparatus according to claim 5, wherein the support cap is comprised of at least one of a thermoplastic, a stainless steel or a combination thereof and has a weight of at least 4 ounces.

11. A method comprising:
a) providing a water supply assembly adjacent an autoclave, wherein the water supply assembly includes:
a support cap, wherein the support cap includes:
a channel therethrough;
an inlet port in operative supported connection with the support cap and in fluid communication with the channel;
a valve assembly in operative supported connection with the support cap and in fluid communication with the channel,
wherein the valve assembly includes a valve, at least one outlet port and a valve actuator,
wherein the support cap has a shape that is configured to cover a reservoir opening into a reservoir of the autoclave,
which autoclave is configured to consume water from the reservoir for use with sanitizing articles placed in the autoclave,
b) passing the valve actuator through the reservoir opening and into the reservoir;
c) placing the support cap on the autoclave so as to be supported by the autoclave and to cover the reservoir opening of the autoclave in a position in which the inlet port is located outside the reservoir,
d) operating the autoclave to cause a decrease in a water level in the reservoir, which causes the valve actuator to open the valve and enable water provided to the inlet port to pass through the channel, out of the at least one outlet port and into the reservoir in order cause an increase in the water level in the reservoir, which increase causes the valve actuator to close the valve and prevent water provided to the inlet port from passing through the channel, out of the at least one outlet port and into the reservoir.

12. The method according to claim 11, wherein the valve actuator includes a float that is buoyant in water,
wherein the float is movable relative to the support cap between:
a first position at which the float causes the valve to close fluid communication between the at least one outlet port and the channel; and
a second position at which the float causes the valve to open fluid communication between the at least one outlet port and the channel, wherein (b) includes passing the float through the reservoir opening and into the reservoir;
wherein (d) includes operating the autoclave to cause the decrease in a water level in the reservoir, which causes the float to move from the first position to the second position, which causes the valve to open and enable water provided to the inlet port to pass through the channel, out of the at least one outlet port and into the reservoir in order cause the increase in the water level in the reservoir, which increase causes the float to move from the second position to the first position, which causes the valve to close and prevent water provided to the inlet port from passing through the channel, out of the at least one outlet port and into the reservoir.

13. The method according to claim 11, wherein prior to (b) the autoclave includes a screen cup extending into the reservoir opening, wherein the reservoir opening has a maximum inner diameter that is between 1.5 and 3.0 inches, further comprising prior to (b) removing the screen cup from reservoir opening to enable the float to be inserted into the reservoir opening in (b).

14. The method according to claim 13, wherein the inlet port is in rotatable connection with the support cap at an axis of rotation, wherein the inlet port includes an inlet port opening that is disposed radially from an axis of rotation, further comprising:
 a) prior to (d) attaching a water supply line to the inlet port;
 b) rotating the inlet port to move a location of the water supply line with respect to the autoclave.

15. The method according to claim 13, wherein the autoclave that the support cap is configured to cover a reservoir opening thereof, includes a housing in which the reservoir is mounted, wherein the housing includes a housing opening adjacent the reservoir opening, wherein the housing opening has a maximum inner diameter that is larger than the maximum inner diameter of the reservoir opening, wherein (c) includes placing the support cap on the autoclave so as to cover both the reservoir opening and the housing opening, wherein in (d) the support cap is configured such that when a water level in the reservoir increases sufficiently to cause the float in the reservoir to move from the second position to the first position, the support cap remains in the position in (c) that covers the opening into the reservoir.

16. The method according to claim 15, wherein the shape of the support cap includes a stepped contour that includes consecutively wider first and second steps, wherein (c) includes placing the support cap on the autoclave such that the first step extends into the reservoir opening.

17. The method according to claim 16, wherein the shape of the support cap includes a stepped contour that includes consecutively wider the first step, the second step, and a third step, wherein when the first step extends into the reservoir opening in (c), the second step extends into the housing opening and the third step covers the housing opening, wherein the second step and is wider than the maximum inner diameter of the reservoir opening, wherein the third step is wider than the maximum inner diameter of the housing opening.

18. The method according to claim 16, wherein in (c) the first step compressively engages with the reservoir opening.

19. The method according to claim 16, wherein in (c) the first step includes at least one annular rib that compressively engages with a neck of the reservoir that surrounds the reservoir opening.

20. The method according to claim 15, wherein in (c) the support cap is comprised of at least one of a thermoplastic, a stainless steel or a combination thereof and has a weight of at least 4 ounces.

* * * * *